(12) United States Patent
Slater et al.

(10) Patent No.: US 7,172,144 B1
(45) Date of Patent: Feb. 6, 2007

(54) SYSTEM FOR MEASURING WEAR IN A GRINDING MILL

(76) Inventors: Dennis Slater, 437 Elisabeth-Turgeon, Rimouski, Québec (CA) G5M 1T7; André Langis, 169 chemin du Sommet Ouest, Rimouski, Québec (CA) G5N 1V4

( * ) Notice: Subject to any disclaimer, the term of this patent is extended or adjusted under 35 U.S.C. 154(b) by 0 days.

(21) Appl. No.: 11/370,981

(22) Filed: Mar. 9, 2006

(51) Int. Cl.
  *B02B 5/02* (2006.01)
  *B02C 13/00* (2006.01)
  *G01N 3/32* (2006.01)

(52) U.S. Cl. .............. 241/101.2; 241/101.3; 241/300; 241/197

(58) Field of Classification Search ............ 241/101.2, 241/101.3, 300, 197, 36, 37; 73/808, 810, 73/811
See application file for complete search history.

(56) References Cited

U.S. PATENT DOCUMENTS

| | | | |
|---|---|---|---|
| 991,421 A | 5/1911 | Brown | |
| 1,772,026 A | 8/1930 | Bartley | |
| 3,582,007 A | 6/1971 | Heighberger | |
| 4,382,253 A | 5/1983 | Belthle | |
| 5,407,141 A | * 4/1995 | Liebing et al. | ................ 241/36 |
| 5,544,819 A | * 8/1996 | Shepherd | ..................... 241/37 |

FOREIGN PATENT DOCUMENTS

JP      354035464 A      3/1979

* cited by examiner

Primary Examiner—Faye Francis
(74) Attorney, Agent, or Firm—Mario Theriault

(57) ABSTRACT

The system for measuring wear in a grinding mill has at least one bolt passing through the shell and a wear plate. The bolt has an elongated oblong-shaped bolt head extending through the wear plate, flush with a surface of the wear plate. The bolt head is exposed to a same abrasion as the wear plate. The bolt has a groove there along and a plurality of wire loops embedded in that groove. Each wire loop extends to a distinct point along the bolt head, such as to form a ruler along the bolt head. A mobile transmitter-receiver is mounted to the stem of the bolt and is connected to the wire loops. The mobile transmitter-receiver has electronic circuitry therein for detecting broken loop conditions and for transmitting these conditions to a remote receiver where the conditions are related to degrees of wear on the wear plate.

20 Claims, 3 Drawing Sheets

SYSTEM FOR MEASURING WEAR IN A GRINDING MILL

FIELD OF THE INVENTION

This invention pertains to a system for measuring wear in a grinding mill for grinding minerals, and more particularly, it pertains to a self-contained measurement and wireless communication device for measuring wear in a grinding mill without stopping the mill.

BACKGROUND OF THE INVENTION

Mining companies grind several thousand tons of ore rocks per days. Generally, the grinding mills used for this task consist of revolving drums which are lined with wear-resistant plates, to resist the abrasion of the ore rocks tumbling against their inside surfaces. These wear plates are replaced periodically when they reach a minimum thickness.

The stopping of one of these mills for inspection represents enormous losses in production time and high energy demand to start it up again. Therefore, there has been numerous efforts made in the past to shorten the inspection time or to reduce inspection frequency to a minimum. For examples;

U.S. Pat. No. 1,772,026 issued to C. O. Bartley on Aug. 5, 1930; discloses a measuring system which consists of one or more screws extending radially through the shell of the mill and into corresponding cavities in one of the wear plates. When the bolt can be inserted further than the bottom of the cavity without resistance, the liner is either broken or has worn to its minimum thickness, and in either cases replacement of the wear plates is in order.

JP Patent 354,035,464 issued to Kubota Ltd., on Mar. 15, 1979, discloses a system wherein the bolts retaining the wear plates have their heads flush with the exposed surfaces of the plates. As a wear plate gets thinner, the bolt heads holding it also wear down. When a bolt head is worn away completely, a spring under the nut of the bolt pulls the nut and the stem of the bolt outside the shell of the mill. The stem and nut fall into a bolt casing and hit a switch in that casing. The switch is connected to a buzzer or other warning device to inform maintenance personnel that a wear plate inside that mill is due for replacement.

Although the systems of the prior art deserve undeniable merits, these systems provide warning when a wear plate is no longer protecting the shell of the mill and the mill must be shut down. These failures can occur during a time of reduced personnel such as a night shift or a holiday. The repair of the mill during these emergency situations is generally done by reduced-size crews and consequently, the mill is unproductive for a longer period than if the repairs would have been carried out during a planned shutdown.

Therefore, there is a need in the industry for a monitoring device which can provide sufficient warning time so that repair work can be schedule ahead, and proper spare parts, tools, rigging and lifting equipment can be brought to the job site in preparation for the job. There is a need for a monitoring device which can provide sufficient warning time to ensure that the repair can be effected quickly, and that the mill can be put back in operation in the shortest possible delay.

SUMMARY OF THE INVENTION

In the present invention, however, there is provided a system for measuring wear to a fraction of an inch for example, and wherein the measurements are transmitted in a wireless mode to a remote receiver, without stopping the mill.

In one aspect of the present invention, there is provided a system for measuring wear in a grinding mill having a shell and at least one wear plate affixed to an inside surface of that shell. The system comprises at least one bolt passing through the shell and the wear plate. The bolt has a bolt head extending through the wear plate, flush with the exposed surface of the wear plate. The bolt head is exposed to a same abrasion as the wear plate, and has a length similar to the usable thickness of the wear plate.

The bolt also has a stem extending through the shell and through the wear plate, and has a groove extending along the stem and the bolt head. At least one wire loop is embedded in that groove. The wire loop extends to a distinct point along the bolt head.

The system also includes a self-contained mobile transmitter-receiver mounted to the stem of the bolt and connected to the wire loop. The mobile transmitter-receiver has electronic circuitry therein for detecting broken loop conditions in the wire loop.

The system also comprises a base transmitter-receiver mounted in a remote location relative to the mill, and a communication system in both the mobile transmitter-receiver and the base transmitter-receiver for transmitting the broken-loop condition to the base transmitter-receiver. The system for measuring wear also includes a computer or other microprocessor for interpreting and relating the broken loop condition to a thickness of the wear plate inside the mill.

The end of the wire loop can be placed at a specific depth along the bolt head, at a depth corresponding to a mid-life thickness of the wear plate for example. The measuring system can be interrogated periodically or continually until the wire loop is broken by abrasion, indicating a specific degree of wear inside the mill. The remaining life of the wear plate can be extrapolated from the operating time on the wear plate prior to the broken loop condition, and the depth of that broken loop. A scheduled shutdown can then be planned and effected at a time that causes minimum disruption to production schedules.

In another aspect of the present invention, there is provided a plurality of wire loops in a same bolt, and the ends of these loops are spaced apart from each other along the bolt head. An electric signal is sent through each loop and each signal is identifiable by a unique frequency, such that each loop, when broken, provides a unique broken loop condition, whereby wear on the bolt head is measurable incrementally.

In yet another aspect of the present invention, a plurality of bolts each having a plurality of wire loops embedded therein and a mobile transmitter-receiver mounted thereon are used to monitor wear at various locations inside the mill.

In yet a further aspect of the present invention, the bolt mentioned above is replaced by a longitudinal probe extending through the thickness of a wear plate. The probe has a plurality of wire loops embedded in a hole along its core. The end of the probe is exposed to wear and the wire loops therein are severed one by one at a same rate as a reduction in thickness of the wear plate in which it is mounted.

This brief summary has been provided so that the nature of the invention may be understood quickly. A more complete understanding of the invention can be obtained by reference to the following detailed description of the preferred embodiment thereof in connection with the attached drawings.

BRIEF DESCRIPTION OF THE DRAWINGS

One embodiment of the present invention is illustrated in the accompanying drawings, in which like numerals denote like parts throughout the several views, and in which.

DESCRIPTION OF THE PREFERRED EMBODIMENT

Figure 1:
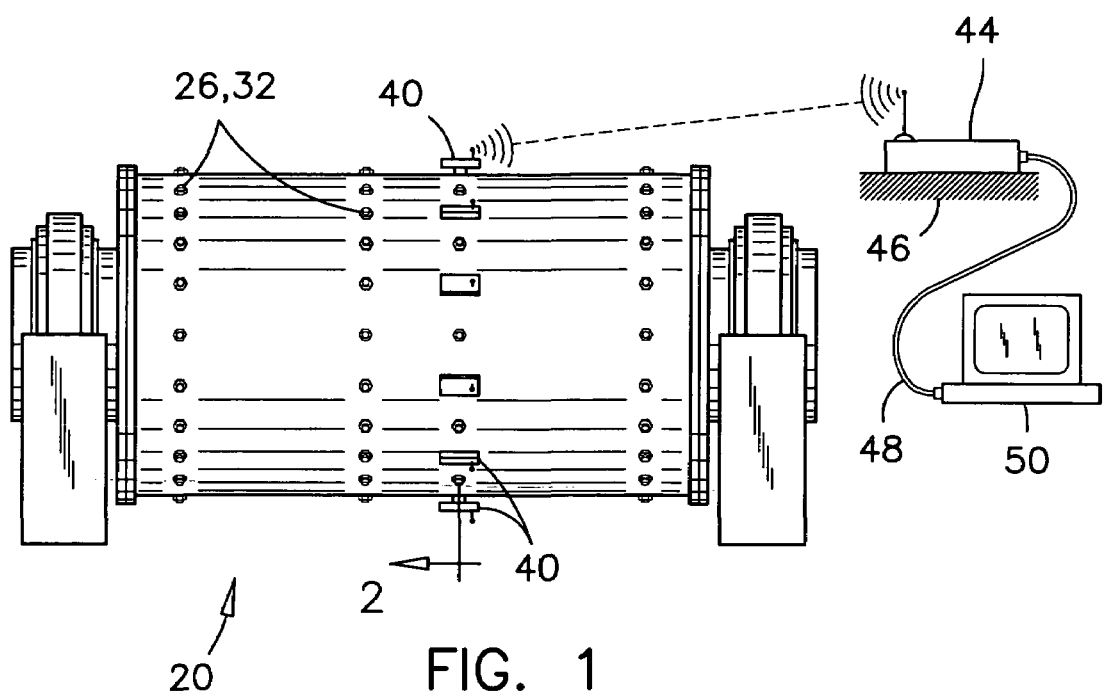
FIG. 1 represents a side view of a grinding mill, having a plurality of wear-plate thickness detectors according to the preferred embodiment of the present invention thereon.

While this invention is susceptible of embodiment in many different forms, there is shown in the drawings and will be described in details herein one specific embodiment of a system for measuring wear in a grinding mill for grinding minerals, or a cement plant. The present disclosure is to be considered as an example of the principles of the invention and is not intended to limit the invention to the embodiment illustrated and described.

Although efforts have been made to limit the use of precise dimensions and exact geometric qualifiers, some narrow expressions remain in this disclosure and are used for convenience only to provide a better understanding of the present invention. Such dimensions and shapes can vary from one model of grinding mill to the other. Therefore the dimensions and geometric expressions mentioned herein should not be considered as being absolute and limiting.

Referring to FIG. 1, a typical grinding mill 20 for grinding minerals is represented therein. It will be appreciated that the illustration in FIG. 1 can also represent a cement mixing plant or other aggregate processing equipment, wherein the present invention would be applicable as well.

Figure 2:
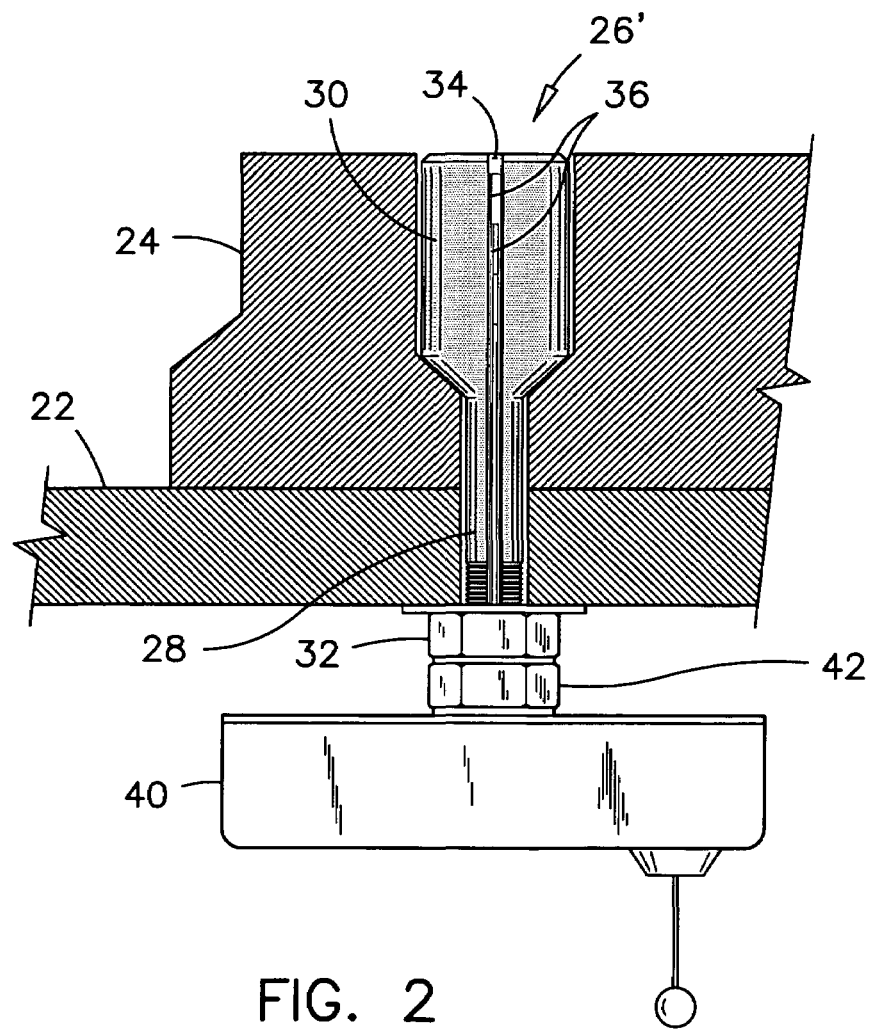
FIG. 2 is a partial cross-section view of a thickness-detector assembly, as seen substantially along line 2 in FIG. 1.

A partial cross-section through the shell 22 of the mill is shown in FIG. 2. The shell's inside surface is lined with wear-resistant plates 24, which are retained to the shell 22 by plate-retaining bolts 26. Each bolt 26 has a round stem 28 and a stretched oblong-shaped head portion 30 which extends flush with the inside surface of the wear plate 24 as illustrated. Each bolt 26 has a threaded stem 28 and a nut 32 mounted on that stem outside the shell 22. A plurality of these bolts 26 and nut 32 retain a plurality of wear plates 24 to the shell 22 of the mill.

In the preferred thickness-detector assembly, each thickness-detector bolt 26' has a longitudinal groove 34 therein. This groove 34 encloses a plurality of wire loops 36, wherein each loop 36 extends to a specific point along the bolt head 30, such as to define a ruler along the bolt head 30.

A self-contained mobile transmitter-receiver 40 is mounted to the outside end of the bolt 26' by means of a threaded coupling 42 mounted to the bolt stem 28, as a locknut against the nut 32. The mobile transmitter-receiver 40 provides power to the wire loops 36, and monitors the response from each loop 36. The response is either an unaltered signal or a lost signal, as in the case of a broken or short circuit.

The mobile transmitter-receiver 40 communicates in a wireless mode to a base transmitter-receiver 44, which is mounted to a fixed structure 46 in vicinity of the mill 20. The base transmitter-receiver 44 is connected by wires 48 to a computer 50, through a RS-232 port for example. Although a fixed base transmitter-receiver 44 as been illustrated, it is also possible to use a handheld electronic device to carry out the same functions, or a base transmitter-receiver mounted inside a laptop computer, for example.

Figures 3, 4:
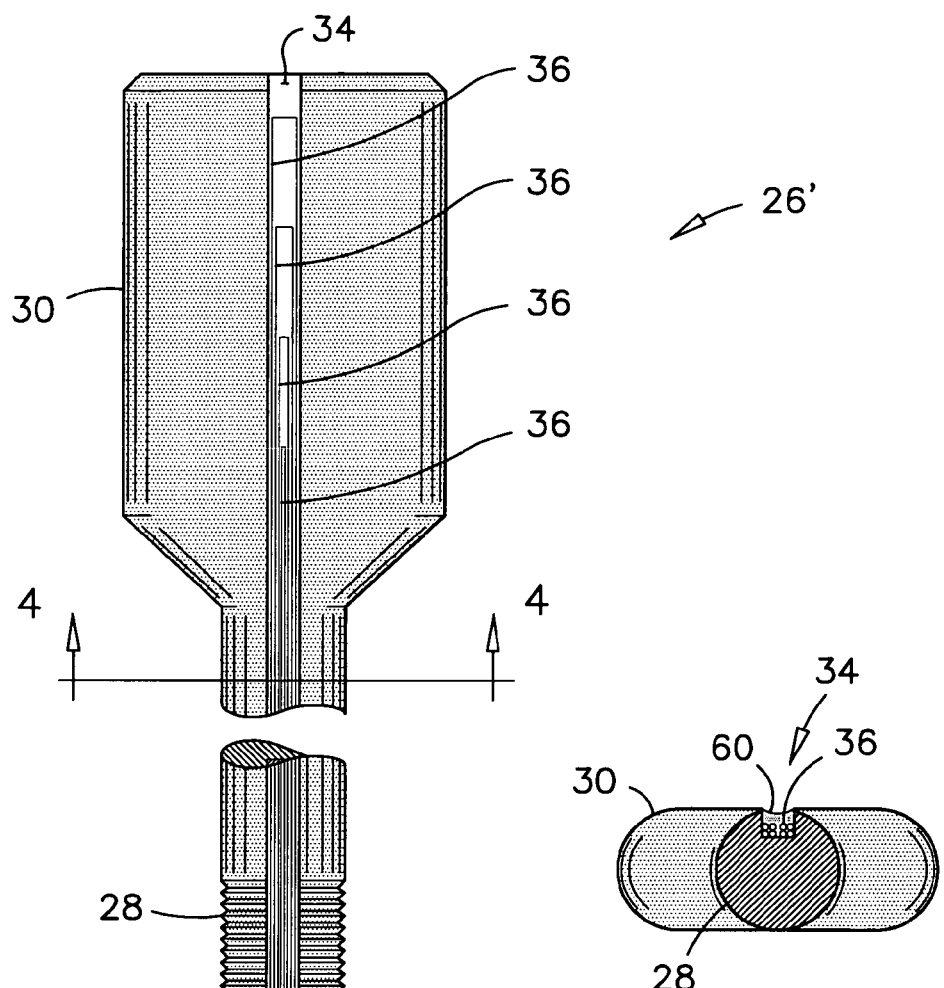
FIG. 3 is a side view of the plate-retaining bolt and a schematic view of a self-contained mobile transmitter-receiver mounted to that bolt.
FIG. 4 is a cross-section view of the plate-retaining bolt as seen along line 4—4 in FIG. 3.

Referring now to FIGS. 3 and 4, the thickness-detector bolt 26' and the mobile transmitter-receivers 40 will be explained in greater details.

The thickness-detector bolt 26' has a plurality of wire loops 36 embedded in the groove 34 there along. The wire loops 36 are embedded in an epoxy 60 or a similar hardened resinous material to keep them in place inside the groove. The wire loops 36 extend to different points along the bolt head 30 of the thickness-detector bolt 26', with the end of each loop being spaced from the other loop ends a specific distance, such as on a ruler, to provide useful information concerning the rate of wear on the wear plates supported by that bolt.

Preferably, the bolt head 30 is made of a material that is softer than the material of the wear plate 24. As the wear plate 24 wears down, the bolt head 30 also wears down at the same rate as the wear plate 24, and the wire loops 36 in that bolt head 30 are broken one by one when they become exposed at the end of the bolt head 30. When a loop 36 is broken, a short-circuit or an open circuit can be detected in that loop 36. The severing of each wire loop 36 provides an indication of the actual thickness of the wear plate 24 at that time. In the preferred embodiment, a large number of wire loops may be used to detect a wear rate to a fraction of an inch for example.

The self-contained mobile transmitter-receiver 40 is built to detect short-circuit to ground or open circuit conditions in each of the wire loops 36. The mobile transmitter-receiver 40 comprises a printed circuit (not shown) and is operated by a battery 62. In use, each wire loop 36 is interrogated by an electrical signal, preferably a square signal, having a unique frequency, to distinguish that loop from other loops. For that purpose, the mobile transmitter-receiver 40 also comprises, a micro-controller 64, connected to both a multiplexer 66 and a decoder 68, with the multiplexer 66 and the decoder 68 being also connected to respective ends of the wire loops 36. Other means of distinguishing one loop from the others can also be used, such other decoding means may include circuitry to pass a current in each loop in sequence or at different time intervals for example.

The base transmitter-receiver 44 also contains a second micro-controller (not shown), which is substantially the same as the first-mentioned one. Both micro-controllers can transmit and receive information to and from each other in a wireless mode.

When more than one bolt-detector 26' and more than one mobile transmitter-receiver 40 are used, all thickness-detector assemblies can be interrogated in sequence or at different time intervals or under different frequencies or by other unique identification codes.

In use, the interrogation of a single thickness-detector assembly 26', 40 is initiated by the computer 50. A first signal is sent to the mobile transmitter-receiver 40 which in turn sends signals to all wire loops 36. The mobile transmitter-receiver 40 reads the condition of each loop 36 and sends this information to the base transmitter-receiver 44 in a wireless mode. The base transmitter-receiver 44 relays this information to the computer 50 wherein the information is interpreted and displayed on the computer screen as an indication of the actual thickness of a wear plate 24 inside the mill. When the thickness of the wear plate reaches a specific measurement, the mill can be scheduled for preventive maintenance and replacement of all the wear plates inside the mill.

The mobile transmitter-receiver 40 and the base transmitted-receiver 44 are explained herein by their functions rather than by their specific structure. The structure of these devices is known to those skilled in the art of communication devices, and therefore, it does not need further explanation.

Figure 6:
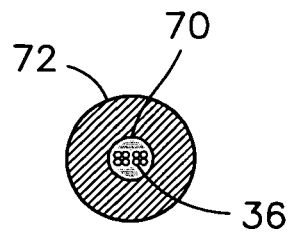
FIG. 6 is a cross-section through the probe shown in FIG. 5, as seen along line 6—6 in FIG. 5.
Figure 5:
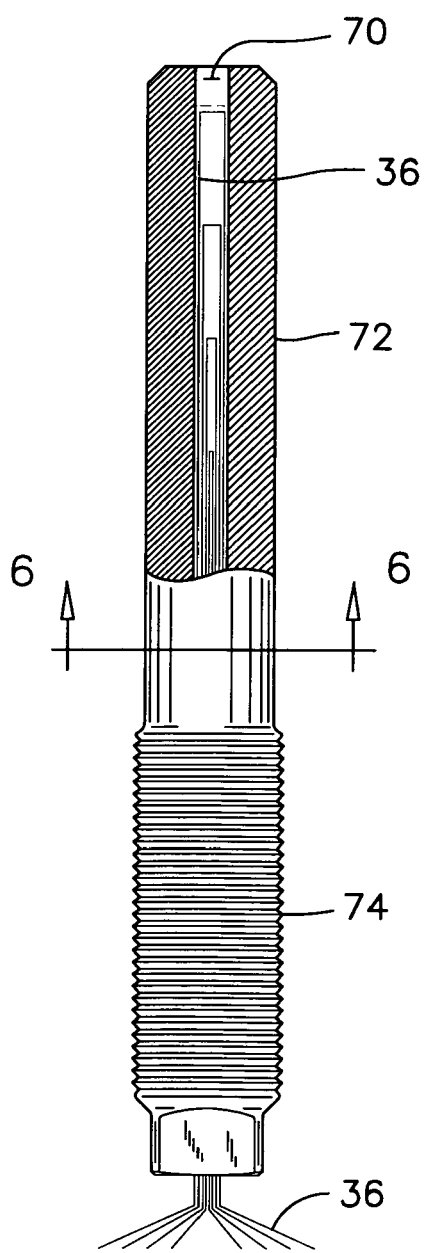
FIG. 5 is a partially cut-away side view of a thickness-measuring probe which can be used as an equivalent for the bolt shown in FIG. 3.

Although a groove 34 in a thickness-detector bolt 26' has been mentioned herein before, it will be appreciated that a hole 70 though the centre of the bolt 26' or through the centre a rod-like probe 72 can also be used, as illustrated in FIGS. 5 and 6. As an example, the probe 72 has a threaded portion 74 that is mountable through the shell 22 of a mill and that is retained thereto by a locknut for example. Other equivalents would include similar probes extending through the thickness of a wear plate, and each having a mounting flange (not shown) or other fastening means for attachment thereof to the shell of a mill.

Figure 7:
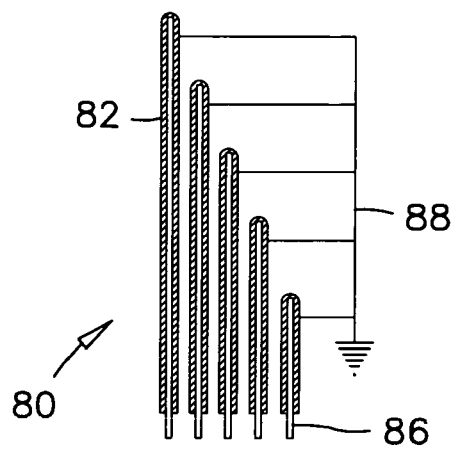
FIGS. 7, 8 and 9 illustrate three different thickness-measuring circuits which can be mounted inside the bolt as shown in FIG. 3, or inside the probe as shown in FIG. 5, for measuring wear in a grinding mill.
Figure 8:
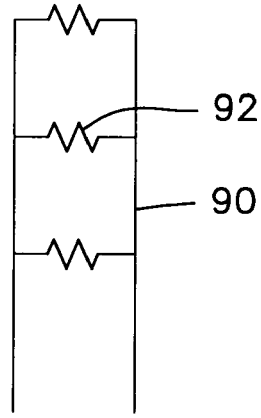
Figure 9:
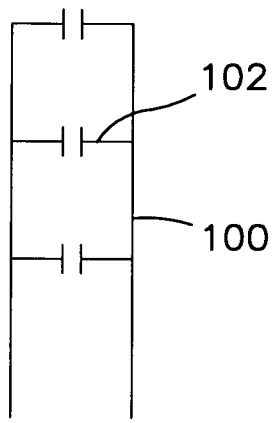

Referring to FIGS. 7, 8 and 9, other equivalents for the wire loops 36 are illustrated. In FIG. 7, the measuring portion of the circuit in the thickness-detector assembly comprises a series of independent insulated wires 80, each extending to a different point along the bolt 26' or probe 72. As wear reaches one wire 80, the insulation 82 is broken and the corresponding bare wire 86 is exposed to the grounded body 88 of the bolt or probe. A grounded signal on one of the wires 82 corresponds to a remaining thickness of the wear plate 24.

In FIG. 8, a single loop 90 with resistors 92 mounted in parallel and at spaced intervals are inserted in the bolt 26' or in a probe 72 and used to detect a degree of wear in a wear plate 24. When a resistor 92 is destroyed from wear, an electric signal in the loop 90 is altered. This signal is interpreted to indicate the remaining length of the bolt 26' or the probe 72.

Similarly, a single loop 100 with capacitors 102 can be mounted inside the bolt 26' or the probe 72 to generate a signal in the loop 100 that is representative of the total capacitance of the loop 100. A variation in that electric signal indicates a different length of the circuit.

As to other manner of usage and operation of the present invention, the same should be apparent from the above description and accompanying drawings, and accordingly further discussion relative to the manner of usage and operation of the invention would be considered repetitious and is not provided.

While one embodiment of the thickness measurement system according to the present invention has been illustrated and described herein above, it will be appreciated by those skilled in the art that various modifications, alternate constructions and equivalents may be employed without departing from the true spirit and scope of the invention. Therefore, the above description and the illustrations should not be construed as limiting the scope of the invention which is defined by the appended claims.

What is claimed is:

1. A system for measuring wear in a mill having a shell and a wear plate affixed to an inside surface of said shell, comprising;
   a probe passing through said shell and said wear plate, said probe having a length extending through said wear plate and said shell, and an end extending flush with an exposed surface of said wear plate; said probe being mounted to said shell such that said end is exposed to a same abrasion as said wear plate;
   said probe also having a passage therein extending there along;
   a wire loop embedded in said passage; said wire loop extending to a distinct point along said probe;
   a mobile transmitter receiver mounted to said probe and being connected to said wire loop; said mobile transmitter-receiver having means for detecting broken loop condition in said wire loop;
   a base transmitter-receiver mounted in a remote location relative to said mill;
   communication means mounted in said mobile transmitter-receiver for transmitting said broken loop condition to said base transmitter-receiver, and
   means associated with said base transmitter-receiver for interpreting and relating said broken loop condition to a thickness of said wear plate.

2. The system as claimed in claim 1, wherein said probe is a bolt having a bolt head extending through said wear plate flush with said exposed surface of said wear plate, and said passage is a groove along a side of said bolt.

3. The system as claimed in claim 1, wherein said wire loop has a plurality of resistors mounted in a parallel and spaced-apart relationship therein.

4. The system as claimed in claim 1, wherein said wire loop has a plurality of capacitors mounted in a parallel and spaced-apart relationship therein.

5. The system for measuring wear as claimed in claim 2, further comprising a plurality of wire loops embedded in said groove, with each of said wire loops extending to a unique point along said bolt head, and means mounted in said mobile transmitter-receiver for interrogating each of said wire loops separately.

6. The system for measuring wear as claimed in claim 5, further comprising an epoxy in said groove covering said wire loops.

7. The system for measuring wear as claimed in claim 2, wherein said bolt has a stem and said stem has a threaded portion and said mobile transmitter-receiver is mounted to said threaded portion of said stem.

8. The system for measuring wear as claimed in claim 5, further comprising means for interrogating each of said wire loops with an electrical signal having a unique frequency.

9. The system for measuring wear as claimed in claim 1, wherein said communication means in said mobile transmitter-receiver for transmitting said broken loop condition to said base transmitter-receiver, comprises means for transmitting in a wireless mode.

10. The system for measuring wear as claimed in claim 1, wherein said means associated with said base transmitter-receiver for interpreting and relating said broken loop condition to a thickness of said wear plate is a handheld electronic device.

11. The system for measuring wear as claimed in claim 2, comprising a plurality of said bolts and a plurality of said mobile transmitter-receivers each having said communication means mounted therein.

12. The system for measuring wear as claimed in claim 11, wherein each of said mobile transmitter-receivers is identifiable by a unique frequency.

13. A system for measuring wear in a mill having a shell and a wear plate affixed to an inside surface of said shell, comprising;
   a bolt passing through said shell and said wear plate, said bolt having a stem extending through said wear plate and said shell, and a bolt head extending through said wear plate flush with a surface of said wear plate and being exposed to a same abrasion as said wear plate; said bolt head having a length similar to a usable thickness of said wear plate;
   said bolt also having a groove extending along said stem and said bolt head thereof;
   a plurality of wire loops embedded in said groove; each of said wire loops extending to a distinct point along said bolt head;
   a mobile transmitter receiver mounted to said stem and being connected to said wire loops; said mobile transmitter-receiver having means for interrogating each of said wire loops separately and for detecting broken loop conditions in said wire loops;
   a base transmitter-receiver mounted in a remote location relative to said mill;
   communication means in said mobile transmitter-receiver for transmitting in a wireless mode said broken loop conditions to said base transmitter-receiver; and
   means associated with said base transmitter-receiver for interpreting and relating said broken loop conditions to a thickness of said wear plate.

14. The system for measuring wear as claimed in claim 13, wherein each of said wire loops is identifiable by a unique frequency.

15. The system for measuring wear as claimed in claim 13, wherein said distinct points define a ruler along said bolt head.

16. A system for measuring wear in a mill having a shell and wear plates affixed to an inside surface of said shell, comprising;
   a plurality of bolts passing through said shell and said wear plates, each of said bolts having a stem extending through one of said wear plates and said shell, and a bolt head extending through said one of said wear plates flush with a surface of said wear plate and being exposed to a same abrasion as said wear plate; each of said bolt head having a length similar to a usable thickness of said wear plates;
   each of said bolt also having a groove extending along said stem and said bolt head;
   a plurality of wire loops embedded in said groove; each of said wire loops extending to a distinct point along said bolt head;
   a plurality of mobile transmitter-receivers, each being mounted to said stem of a respective one of said bolts and being connected to said wire loops along said groove in said respective one of said bolts; said mobile transmitter-receiver having means for interrogating each of said wire loops in said respective one of said bolts separately and for detecting broken loop conditions in said wire loops;
   a base transmitter-receiver mounted in a remote location relative to said mill;
   communication means in each of said mobile transmitter-receiver for transmitting in a wireless mode said broken loop conditions to said base transmitter-receiver, and
   means associated to said base transmitter-receiver for interpreting and relating said broken loop conditions to a thickness of said wear plates.

17. The system for measuring wear as claimed in claim 16, wherein each of said wire loops and each of said mobile transmitter-receivers are identifiable by a unique frequency.

18. The system for measuring wear as claimed in claim 16, further comprising epoxy covering said wire loops in each of said grooves.

19. The system for measuring wear as claimed in claim 16, wherein each of said stems has a threaded portion and each of said mobile transmitter-receiver is mounted to said threaded portion on a respective one of said stems.

20. The system for measuring wear as claimed in claim 16, wherein said distinct points define a ruler along said bolt head.

* * * * *